United States Patent [19]

Bohn et al.

[11] Patent Number: 4,500,451

[45] Date of Patent: Feb. 19, 1985

[54] NEW PROTEIN PP$_{13}$ EXTRACTED FROM HUMAN PLACENTAL TISSUES AND USE THEREOF

[75] Inventors: Hans Bohn, Marburg; Walter Kraus, Cölbe, both of Fed. Rep. of Germany

[73] Assignee: Behringwerke Aktiengesellschaft, Marburg, Fed. Rep. of Germany

[21] Appl. No.: 524,201

[22] Filed: Aug. 18, 1983

[30] Foreign Application Priority Data

Aug. 20, 1982 [DE] Fed. Rep. of Germany ....... 3230996

[51] Int. Cl.$^3$ .................... A23J 1/06; C07K 7/00; C07G 7/26; A61K 39/00
[52] U.S. Cl. ...................... 260/112 R; 260/112 B; 424/85; 424/88
[58] Field of Search ............... 260/112 R, 112 B; 424/95, 105, 85, 88

[56] References Cited

U.S. PATENT DOCUMENTS

| | | | |
|---|---|---|---|
| 4,041,021 | 8/1977 | Bohn | 260/112 B |
| 4,254,021 | 3/1981 | Bohn et al. | 260/112 B |
| 4,348,316 | 9/1982 | Bohn | 260/112 R |
| 4,368,148 | 1/1983 | Bohn | 260/112 B |

OTHER PUBLICATIONS

Bohn et al., Chemical Abstract, vol. 99, No. 508SH, 1983, "Purification and Characterization of Two New Soluble Placental Tissue Proteins PP$_{13}$ and PP$_{17}$" *Oncodevelopmental Biology and Medicine.*

*Primary Examiner*—Thomas G. Wiseman
*Assistant Examiner*—Robin Lyn Teskin
*Attorney, Agent, or Firm*—Finnegan, Henderson, Farabow, Garrett & Dunner

[57] ABSTRACT

Protein PP$_{13}$ is isolated from human placental tissues using a variety of methods, e.g., immunoadsorption. The protein has utility in production of an antiserum which has diagnostic applications. The placental specific proteins (e.g., PP$_{13}$) are frequently detected in increasing amounts in women as pregnancy advances, and in patients with tumors especially of the tryphoblastic and embryonal types.

3 Claims, 2 Drawing Figures

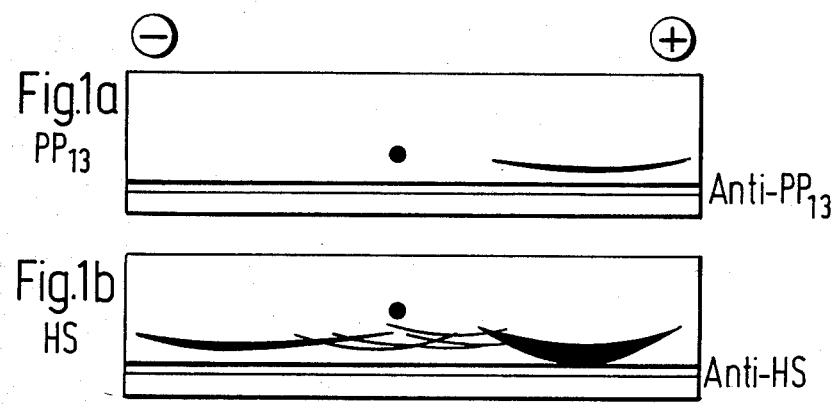

NEW PROTEIN PP$_{13}$ EXTRACTED FROM HUMAN PLACENTAL TISSUES AND USE THEREOF

The invention relates to a new protein (PP$_{13}$), a process for enriching and isolating it from an extract of human placentae and its use.

A number of soluble proteins originating from human placentae have already been detected in the extract of this tissue (Bohn, H., Placental and Pregnancy Proteins, in Carcino-Embryonic Proteins, Vol. I, Ed., F.G. Lehmann, Elsevier/North-Holland Biomedical Press, 1979).

The present invention describes the isolation and characterization of a new soluble protein which is called PP$_{13}$.

The invention relates to the protein PP$_{13}$ which is characterized by (a) an electrophoretic mobility in the same range as albumin, (b) an isoelectric point of $4.75 \pm 0.15$, (c) a sedimentation coefficient $S_{20}^{0}{,}_w$ of $3.1 \pm 0.15$, (d) a molecular weight determined by ultracentrifugation of $30{,}000 \pm 5{,}000$, (e) a molecular weight determined in a polyacrylamide gel containing sodium dodecyl sulfate (SDS) of $29{,}000 \pm 3{,}000$, (f) an extinction coefficient $E_{1cm}$ (280 nm) of $9.8 \pm 0.3$, and (g) a carbohydrate content of 21 1% (g/100 g) (mannose $0.1 \pm 0.05\%$, galactose $0.2 \pm 0.1\%$, xylose $0.1 \pm 0.05\%$, glucosamine $0.2 \pm 0.1\%$, neuraminic acid not detected).

The aminoacid composition of PP$_{13}$ is shown in the table below:

| | Aminoacid composition of PP$_{13}$ | |
|---|---|---|
| | (Residues per 100 residues) mole % | Coefficient of variation |
| Lysine | 4.97 | 11.45 |
| Histidine | 2.28 | 31.46 |
| Arginine | 4.38 | 2.87 |
| Aspartic acid | 12.60 | 4.65 |
| Threonine | 3.94 | 6.05 |
| Serine | 7.83 | 5.96 |
| Glutamic acid | 10.16 | 2.54 |
| Proline | 5.53 | 5.53 |
| Glycine | 6.13 | 4.72 |
| Alanine | 3.39 | 2.49 |
| Cystine ½ | 3.73 | 2.93 |
| Valine | 9.85 | 6.79 |
| Methionine | 2.09 | 13.3 |
| Isoleucine | 6.11 | 3.79 |
| Leucine | 5.87 | 0.50 |
| Tyrosine | 3.88 | 4.56 |
| Phenylalanine | 5.68 | 6.85 |
| Tryptophan | 1.46 | 3.09 |

In order to illustrate the characterizing features of the tissue protein, the following may be said:

The investigation of the electrophoretic mobility was carried out in the micromodification using the Microzone R 200 equipment from Beckman Instruments on cellulose acetate films (supplied by Sartorius) using sodium diethyl barbiturate buffer, pH 8.6.

The isoelectric point was determined with a column (440 ml) supplied by LKB, Stockholm. In the investigation of the glycoprotein, the so-called Ampholine$^{(R)}$ mixture had a pH range of 4.0 to 6.0.

The sedimentation coefficient was determined in an analytical ultracentrifuge supplied by Beckman (Spinco apparatus, model E) at 60,000 rpm in double-sector cells using the UV scanner technique at 280 nm. The solvent used was a 0.05 M phosphate buffer (pH 6.8) which contained 0.2 mole/liter of NaCl. The protein concentration was adjusted to an optical density (O.D.) of about 3. The calculated sedimentation coefficient was based on water at 20° C.

In order to determine the molecular weight by ultracentrifugation, the sedimentation equilibrium method was employed. The concentration of the protein in this was adjusted to about 1.0 O.D.. The determination was carried out at 9,000 rpm. The recording was carried out using UV optics at 280 nm employing a photoelectric scanner.

In order to determine the molecular weight in a SDS-PAA gel, a 7.5% (g/100 ml) polyacrylamide (PAA) gel which contained 0.1% (g/100 ml) of sodium dodecyl sulfate (SDS) was used. The comparison substances used were human placental lactogen (HPL) and human albumin and its aggregates.

In order to determine the extinction coefficient, the substance was dissolved at a concentration of 0.10% (g/100 ml) in distilled water.

The analysis of the carbohydrates was carried out as follows: after hydrolysis of the glycosidic bonds, the liberated neutral sugars were separated as borate complexes on an anion exchange column (Y.C. Lee et al., Anal. Biochem. 27, 567 (1969)), underwant a color reaction in the eluate by adding Cu(I) bicinchoninate reagent (K. Mopper and M. Gindler, Anal. Biochem. 56, 440 (1973)), and were quantitatively determined using rhamnose as an internal standard. The amino sugars were detected and determined by their reaction with ninhydrin. The content of neuraminic acid was found by the method of Warren (Methods in Enzymology, Vol. VI, 463–465 (1963)).

The aminoacid analysis was carried out by the method of S. Moore, D. H. Spackman, W. H. Stein, Anal. Chem. 30, page 1185 (1958) using the Multichrome B liquid chromatograph supplied by Beckman. ½ cystine was determined as cysteic acid after oxidation of the proteins with performic acid (S. Moore et al., Anal. Chem. 30, page 1185 (1958)) and subsequent chromatography (S. Moore, J. Biol. Chem., 238, page 235 (1963)). The content of tryptophane was found by direct photometric determination by the method of H. Edelhoch, Biochemistry 6, page 1948 (1967).

PP$_{13}$ has the following properties which can be used in a process for its isolation by employing methods appropriate for these properties:

(1) It is precipitated from aqueous solutions with ammonium sulfate at pH 7.0 and 30–60% saturation.

(2) It is precipitated with water-soluble acridine bases, for example 2-ethoxy-6,9-diaminoacridine lactate (Rivanol$^{(R)}$) at pH values between 4 and 9 and at a concentration of base of 0.2 to 0.8% (g/100 ml).

It is partially precipitated at a pH of 6.0 and a concentration of Rivanol of 0.4% (g/100 ml).

(3) Its mobility on electrophoretic separation at pH 8.0 resembles that of albumin.

(4) On isoelectric focusing, it appears in the pH range from 4.6 to 4.9 with a maximum 4.7 and 4.8.

(5) On gel filtration with Sephadex$^{(R)}$, it behaves like proteins having molecular weights from 10,000 to 40,000.

(6) It can be bound to weakly basic ion exchangers, such as, for example, DEAE cellulose or DEAE sephadex, at a conductivity of about 0–2 mS and a pH of about 7 to 9, and it is only eluted again from the ion exchanger using highly concentrated salt solutions (1–5 g/100 ml NaCl solutions).

(7) It can be enriched and isolated from an aqueous solution by immunoadsorption.

The invention also relates to a process for isolating $PP_{13}$ which comprises fractioning an extract of human placentae using the above properties.

Obviously, apart from ammonia sulfate, other neutral salts customarily employed in preparative biochemistry can be used to precipitate $PP_{13}$. Apart from an acridine base, a water-soluble derivative of a quinoline base, as are known for protein fractionation, can be employed within the scope of the process according to the invention. In accordance with its electrophoretic behavior, its isoelectric point and its molecular weight, other methods which are suitable for separating a protein having the indicated properties from other proteins can also be used to isolate the protein. The various methods of preparative electrophoresis, isoelectric focusing, gel filtration, gel chromatography or ultrafiltration or even the property of $PP_{13}$ of being able to bind to weakly basic ion exchangers and be eluted off again can be used for this purpose.

$PP_{13}$ can be isolated by appropriate combination of the methods mentioned which bring about an enrichment of $PP_{13}$ or separation of this protein from other proteins.

Accordingly, the present invention is to be seen as relating to the individual steps for the enrichment of $PP_{13}$ and to process for the purification of $PP_{13}$ resulting from a combination of the methods for enrichment.

The steps for the enrichment and isolation of $PP_{13}$ indicated in the example are by no means all mandatory and, moreover, need not be carried out in the sequence described in the example.

The extract from human placentae can be employed directly for immunoadsorption. However, since the concentration of $PP_{13}$ in the placental extract is relatively low, it is advantageous, by preliminary fractionation of the extract, first specifically to enrich the protein $PP_{13}$ using methods which are suitable for the fractionation of proteins on a relatively large scale; for example by fractional precipitation with neutral salts or organic cations, by gel filtration or by ion exchange chromatography. It would also be possible to replace the immunoadsorptions by using other methods of separation, for example by preparative electrophoresis and isoelectric focusing.

Gel filtration on Sephadex G 100 and inverse immunoadsorption have proved to be utilized in the final stage of isolation for the production of highly pure $PP_{13}$.

On average, using physiologic saline, 3.7 mg of this protein can be extracted from a fully developed human placenta (600 g). Extracts of other human organs (for example the heart, lung, skin, stomach, kidneys, uterus, liver, spleen, adrenals, colon and bladder) either do not contain this protein or contain it in considerably lower concentrations. Moreover, $PP_{13}$ normally occurs not at all or only in traces (<1 mg/liter) in the sera of other human body fluids.

For the detection and determination of $PP_{13}$, for example in a fraction from a separating operation, apart from the indicated parameters, immunochemical methods can also be used, since $PP_{13}$ has antigenic properties. Specific antibodies are formed on immunizing animals with this protein.

An antiserum which can be used for this purpose can be obtained as follows: a polyvalent antiserum is obtained by immunizing rabbits with a placental protein fraction containing $PP_{13}$ (for example a mother liquor from the crystallization of human placental lactogen (HPL) by the method of Bohn H., Experientia 27 (1971) 1223), and this antiserum contains, inter alia, antibodies against $PP_{13}$. This antiserum can be made highly specific for the antigen $PP_{13}$ by absorption with normal human serum and those placental fractions which do not contain $PP_{13}$, or with purified placental proteins (for example HPL, $PP_{11}$, $PP_{12}$ and $PP_{16}$).

On the one hand, this antiserum can be used for the immunologic determination of $PP_{13}$ and, on the other hand, for the preparation of an immunoabsorbent which can be employed for enriching and isolating $PP_{13}$.

Monospecific antisera can be prepared by immunizing animals by known methods using the purified $PP_{13}$ obtained by the method in the present Application.

FIG. 1a shows the immunologic reaction of $PP_{13}$ with a specific rabbit antiserum after separation in an electric field on agar-containing gel.

For the purpose of comparison with this, FIG. 1b shows the separation of the proteins in the serum rendered visible by their immune reaction with a rabbit antiserum against human serum (HS).

The Ouchterlony gel diffusion technique can also be used for the immunologic detection of $PP_{13}$ (cf. Schultze and Heremans, Molecular Biology of Human Proteins, vol. 1 page 134) or, if necessary, more sensitive methods, such as radioimmunoassays or enzyme immunoassays.

The detection and determination of $PP_{13}$ have diagnostic significance: $PP_{13}$ is a protein which is "specific" to the placenta. Proteins of this type are generally found in increasing amounts in the serum as pregnancy advances; thus they can be used as parameters for monitoring pregnancy. On the other hand, placenta-specific proteins can frequently also be detected in the serum of patients with tumors, particularly with trophoblastic and embryonal tumors, or are localized in the tissue of the tumors; thus they can be used in diseases of this type as markers for monitoring the progress of the disease and for monitoring therapy.

Thus, $PP_{13}$ can be used to prepare antisera which can be used to detect and determine $PP_{13}$.

The invention is illustrated by the example which follows:

Example (A) Extraction of the placentae and fractionation of the extract with Rivanol and ammonium sulfate 1,000 kg of deep-frozen human placentae were reduced in size in a cutting mixer and extracted with 1,000 liters of a 0.4% strength (g/100 ml) saline solution. After removal of the residual tissue by centrifugation, the extract was adjusted to pH 6.0 with 20% strength (g/100 ml) acetic acid, and 200 liters of a 3% strength (g/100 ml) solution of 2-ethoxy-6,9-diaminoacridine lactate (Rivanol(R), Hoechst AG) were added, with stirring. The precipitate was removed by centrifugation, 500 liters of a 2.5% strength (g/100 ml) NaCl solution were added and the mixture was stirred for 4 hours. The precipitated chloride of 2-ethoxy-6,9-diaminoacridine was removed by centrifugation. Sufficient solid ammonium sulfate was slowly added to the supernatant, with stirring, until a final concentration of 30% (g/100 ml) was reached. The precipitate was removed by centrifugation. This produced 4.5 kg of a moist paste which is denoted fraction A in the following text.

(B) Gel filtration on Sephadex G-150

1,200 g of fraction A were dissolved in water and dialyzed against a 0.01 M tris-HCL buffer (pH 8.0) which contained 0.05% (g/100 ml) of $NaN_3$ (buffer solution I). The remaining solution was applied to a column (60×65 cm) filled with Sephadex G-150 and eluted with buffer solution I. The eluates containing the low molecular weight proteins (MW 10,000–40,000) were combined and are denoted fraction B.

(C) Chromatography on DEAE cellulose

The proteins in fraction B were adsorbed on DEAE cellulose (column 10×28 cm). The column was then washed with buffer solution I and eluted with 5% (g/100 ml) saline solution. The eluate was reduced in volume by ultrafiltration and dialyzed against a 0.1 M tris-HCl buffer of pH 8 which contained 1 mole/liter of NaCl and 0.1% sodium azide (buffer solution II) (fraction C).

(D) Enrichment of $PP_{13}$ immunoadsorption

1. Preparation of the immunoadsorbent 400 ml of a rabbit anti-$PP_{13}$ serum were dialyzed against 0.02 M phosphate buffer (pH 7.0) and chromatographed on DEAE cellulose to remove the immunoglobulins. The immunoglobulin fraction (4.69 g of protein) was then reacted with 469 g of specially purified agarose in the form of beads (Sepharose$^{(R)}$ from Pharmacia, Uppsala, Sweden) which had been activated with 58.6 g of cyanogen bromide, and thus covalently bonded to a support. The procedure has been described by Axen R., Porath J., Ernbach S., Nature 214, 1302 (1967). It was possible to isolate $PP_{13}$ from solutions containing it, especially from placental extract fractions enriched in $PP_{13}$, using an immunoadsorbent prepared in this manner.

2. Immunoadsorption

The immunoadsorbent was suspended in buffer solution II, introduced into a chromatography column (5.5×22 cm) and washed with buffer solution II. Then fraction C was applied to the column, the $PP_{13}$ being bound by immunoadsorption. The column was then thoroughly washed with buffer II; the adsorbed protein was then eluted from the column using about 600 ml of 3 M potassium thiocyanate solution. The eluates containing $PP_{13}$ were dialyzed against buffer solution II and reduced in volume to about 20 ml by ultrafiltration. The yield per adsorption was about 10 mg of $PP_{13}$. Immediately after the elution of $PP_{13}$, the adsorbent in the column was neutralized again with buffer solution II and thoroughly washed; it was then used again for binding $PP_{13}$ by immunoadsorption.

(E) Production of highly pure $PP_{13}$

The protein obtained by immunoadsorption was frequently contaminated with non-specifically bound serum proteins and other placental tissue proteins. The removal of the major part of the accompanying serum proteins was achieved by gel filtration on Sephadex G-100. The remaining accompanying proteins were then removed by inverse or negative immunoadsorption, that is to say using carrier-bond antibodies against the proteins still present as impurities (HPL, $PP_{12}$, $PP_{16}$ and serum proteins.)

We claim:

1. A new placental protein $PP_{13}$ extracted from human placental tissue characterized by the following:
    (a) an electrophoretic mobility in the same range as albumin,
    (b) an isoelectric point of 4.75±0.15,
    (c) a sedimentation coefficient $S_{20}^0{}_{,w}$ of 3.1±0.15,
    (d) a molecular weight determined by ultracentrifugation of 30,000±5,000,
    (e) a molecular weight determined in a polyacrylamide gel containing sodium dodecyl sulfate (SDS) of 29,000±3,000,
    (f) an extinction coefficient $E_{1cm}{}^{1\%}$ (280 nm) of 9.8±0.3 and
    (g) a carbohydrate content of 1% (0.1±0.05% mannose, 0.2±0.1% galactose, 0.1±0.05% xylose, 0.2±0.1% glucosamine, and neuraminic acid not detected).

2. An antiserum specific to $PP_{13}$ obtained by immunizing an animal with protein $PP_{13}$ and recovering serum containing antibodies to said protein.

3. A process for purifying protein $PP_{13}$ comprising: (1) binding an antiserum specific to protein $PP_{13}$ to a substrate; (2) introducing a sample containing $PP_{13}$ onto said substrate; and (3) eluting the protein $PP_{13}$ from said substrate.

* * * * *